US00PP15581P2

(12) United States Plant Patent
Trees

(10) Patent No.: US PP15,581 P2
(45) Date of Patent: Feb. 22, 2005

(54) ***VERBENA* PLANT NAMED 'BALAZGAGIC'**

(50) Latin Name: *Verbena×hybrida*
Varietal Denomination: Balazgagic

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 33 days.

(21) Appl. No.: 10/741,697

(22) Filed: Dec. 19, 2003

(51) Int. Cl.[7] ..... A01H 5/00
(52) U.S. Cl. ..... Plt./308
(58) Field of Search ..... Plt./308

*Primary Examiner*—Anne Marie Grunberg
(74) *Attorney, Agent, or Firm*—Wood, Phillips, Katz, Clark & Mortimer

(57) ABSTRACT

A new and distinct cultivar of *Verbena* plant named 'Balazgagic' characterized by its purple-colored flowers, cleft, dark green-colored foliage, basal branching character, and spreading and trailing growth habit.

2 Drawing Sheets

Latin name of genus and species of plant claimed: *Verbena×hybrida.*
Variety denomination: 'Balazgagic'.

BACKGROUND OF THE INVENTION

The present invention relates to a new and distinct *Verbena* plant botanically known as *Verbena×hybrida* and hereinafter referred to by the cultivar name 'Balazgagic'.

The new cultivar was developed by the inventor through a controlled breeding program during September 2001 at Arroyo Grande, Calif. The objective of the breeding program was the development of *Verbena* cultivars with attractive flower coloration, continuous flowering and semi-trailing growth habit.

The female (seed) parent of 'Balazgagic' was the proprietary *Verbena×hybrida* cultivar designated '1036-2' (not patented), which exhibits a prostrate, trailing habit, white-colored flowers and dark green foliage. The male (pollen) parent of 'Balazgagic' was the commercially available *Verbena* cultivar 'Splash Violet' (not patented), which exhibits an upright habit, white-colored flowers with purple spots and medium green foliage. The new cultivar was discovered and selected by the inventor as a single flowering plant from within the progeny of the above stated cross-pollination during July 2002 at Arroyo Grande, Calif.

Asexual reproduction of the new cultivar, by terminal stem cuttings since 2002 at West Chicago, Ill. has demonstrated that the new *Verbena* reproduces true to type, with all the characteristics as herein described, firmly fixed and retained through successive generations of such asexual propagation.

SUMMARY OF THE INVENTION

The new cultivar has not been observed under all possible environmental conditions to date. Accordingly, it is possible that the phenotype may vary somewhat with variations in the environment, such as temperature, light intensity, and day length without, however, any change in genotype.

It was repeatedly found that the cultivar of the present invention:

1. Exhibits purple-colored flowers.
2. Forms cleft, dark green-colored foliage,
3. Exhibits a good basal branching character, and
4. Exhibits a mounded and trailing growth habit.

Plants of the new cultivar differ from plants of the female parent primarily in flower color and from plants of the male parent primarily in growth habit.

The new cultivar of the present invention can be compared to the cultivar Superbena™ Dark Blue (not patented). However, in side-by-side comparisons conducted in West Chicago, Ill., plants of the new cultivar differed from plants of Superbena™ Dark Blue primarily in flower color. Plants of the new cultivar have flowers of a lighter purple-color than plants of Superbena™ Dark Blue.

BRIEF DESCRIPTION OF THE PHOTOGRAPH

The accompanying photographs show as nearly true as it is reasonably possible to make the same in color illustrations of this type, typical flower and foliage characteristics of the new cultivar. Colors in the photographs differ slightly from the color values cited in the detailed description, which accurately describe the colors of 'Balazgagic'. The plants were grown in a greenhouse for 10 weeks in West Chicago, Ill.

DETAILED BOTANICAL DESCRIPTION

Figure 1:
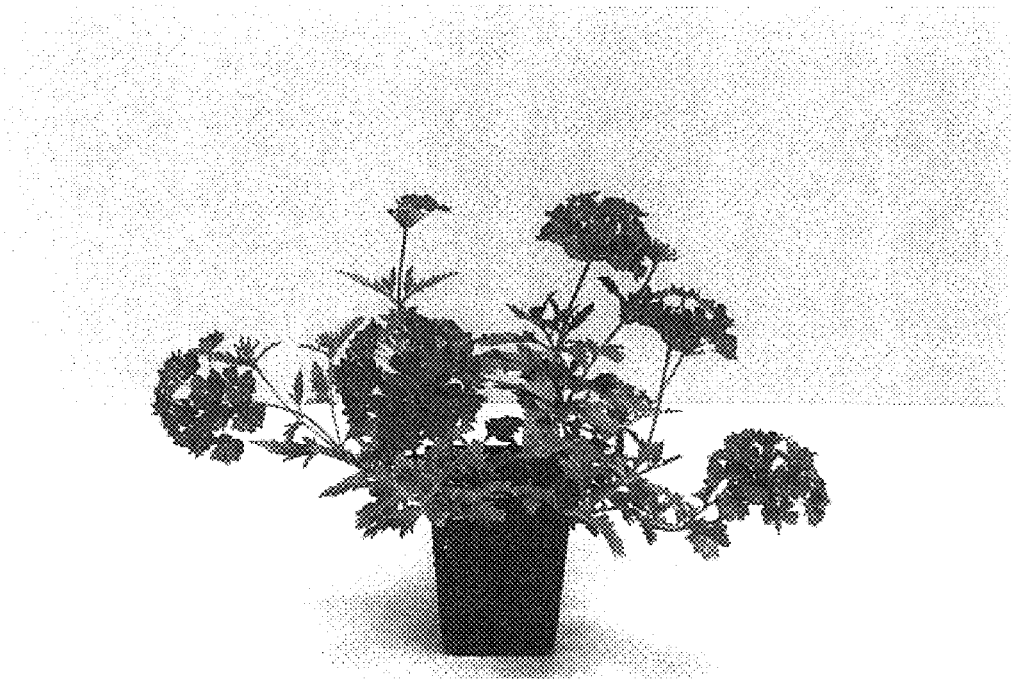
FIG. 1 illustrates a side view of the overall growth and flowering habit of 'Balazgagic'.
Figure 2:
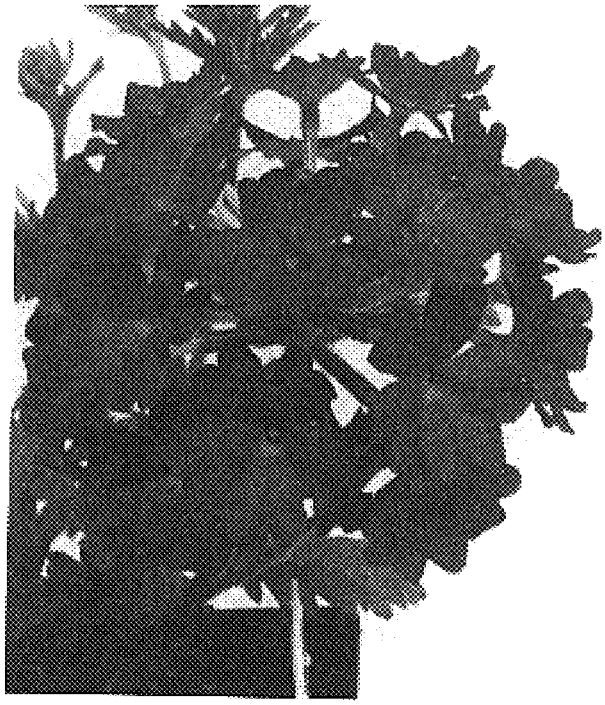
FIG. 2 illustrates a close-up view of a single inflorescence of 'Balazgagic'.
Figure 3:
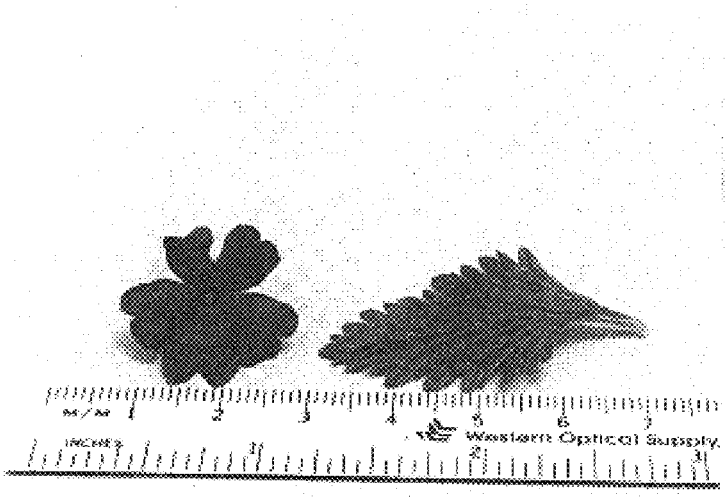
FIG. 3 illustrates a close-up view of an individual flower and leaf of 'Balazgagic'.

The chart used in the identification of colors described herein is The R.H.S. Colour Chart of The Royal Horticultural Society, London, England, 1995 edition, except where general color terms of ordinary significance are used. The color values were determined on Jul. 21, 2003. The readings were taken between 10:30 and 11:30 a.m. under natural daylight conditions. The plants used for the following descriptions and measurements were produced from cuttings taken from stock plants and were grown in a double polycarbonate-covered greenhouse under conditions comparable to those used in commercial practice. The plants were grown in 10 cm pots for 10 weeks while utilizing a soilless growth medium. Greenhouse temperatures were maintained at approximately 70°–80° F. during the day and approximately 62°–65° F. during the night. Greenhouse light levels were maintained at 5,000–8,000 footcandles during the day.

Classification:

*Botanical.*—*Verbena×hybrida* cultivar 'Balazgagic'.

Parentage:

*Female parent.*—Proprietary *Verbena×hybrida* selection designated '1036-2' (not patented).

*Male parent.*—Commercially available *Verbena* cultivar Splash Violet (not patented).

Propagation:

*Type cutting.*—Terminal tip.

*Time to initiate roots.*—Approximately 14–21 days.

*Root description.*—Fine, fibrous.

*Rooting habit.*—Freely branching.

Plant description:

*General appearance and growth habit.*—Spreading and trailing. Moderately vigorous with good basal branching. Pinching improves basal branching. A mature plant, 10 weeks after the planting of a rooted cutting, commonly measures approximately 14.4 cm from soil level to top of plant plane and approximately 38 cm in diameter (area of spread).

*Branch description.*—Shape: Tetragonal. Diameter: Approximately 2.2 mm. Texture: Densely pubescent. Color: Slightly darker than 144A. Internode length at middle of branch: Approximately 2.9 cm.

*Foliage.*—Type: Simple. Arrangement: Opposite. Shape: Ovate. Margin: Cleft. Apex: Broadly acute. Base: Attenuate. Texture: Densely covered with short stiff hairs on upper and lower surfaces, especially along veins on lower surface. Venation pattern: Pinnate. Leaf length: Approximately 4 cm. Leaf width: Approximately 2.6 cm at widest point. Color of upper surface of mature leaf: Slightly darker than 137A with venation of 144C. Color of lower surface of mature foliage: 147B with venation of 144C. Petiole: Length: Approximately 1 cm. Diameter: Approximately 2 mm. Texture: Upper and lower surface: Moderately pubescent with short stiff hairs. Color of upper and lower surface: 144C.

Flowering description:

*Flowering habit.*—Freely flowering under outdoor growing conditions with substantially continuous blooming from spring through fall. Year round in greenhouse environment.

*Time to first flower.*—Approximately 5–7 weeks from planting of rooted cutting.

*Lastingness of bloom.*—Approximately 3–4 days.

Inflorescence description:

*Type.*—Hemispherical corymb positioned above and beyond foliage. Quantity: Approximately 7 per plant open at any one time. Height: Approximately 3.4 cm. Width: Approximately 6 cm. Quantity of flowers: Approximately 13 fully opened flowers per inflorescence at any one time.

*Penduncle.*—Length: Approximately 4.1 cm. Diameter: Approximately 1.1 mm. Texture: Densely pubescent with short stiff hairs. Color: Slightly darker than 144A.

Flower description:

*Type.*—Single, salverform, not fragrant, persistent.

*Bud.*—Shape: Spherical. Length: 2.5 mm. Diameter: Approximately 2 mm. Color just before opening: N82A.

*Flower diameter.*—Approximately 2.2 cm. Corolla tube length: Approximately 2.1 cm. Tube diameter at opening: 1.8 mm. Tube diameter at base: 1.2 mm.

*Petals.*—Quantity: Five per flower, fused at base, somewhat overlapping. Shape: Obovate. Apex: Emarginate. Margin: Entire. Texture of upper and lower surface: Glabrous. Color of upper surface: When opening N81A. When fully opened N82A. Fading to N89C. Color of lower surface when fully opened: N82D. Whiskers of N82B surround the opening of the corolla tube.

*Corolla tube.*—Outside surface: Texture: Pubescent. Color: 149D. Inner Surface: Texture: Pubescent around anthers. Color: 149D.

*Calyx.*—Quantity of sepals: 5, fused into a tube. Tube description: 5 toothed, 5 ribbed, with stipules. Tube length: Approximately 1.2 cm. Tube diameter at base: Approximately 1 mm. Diameter at apex: Approximately 2 mm. Texture: Densely glandular. Color: 93A.

*Reproductive organs.*—Stamens: Quantity: 4 per flower. Position of stamens: Two above anthers, two even with anthers. Anther shape: Ovoid. Anther length: 1.5 mm. Anther color: 151C. Pollen amount: Sparse. Pollen color: 8C. Pistil: Quantity: One per flower. Pistil length: 2.1 cm. Stigma shape: Bi-lobed, funnel shaped. Stigma length: 3 mm. Stigma color: N144C. Style length: 1.6 cm. Style color: 145B. Ovary diameter: 1.5 mm. Ovary color: N144C.

Seed and fruit production: Neither seed nor fruit production has been observed.

Disease and pest resistance: Resistance to pathogen and pests common to *Verbena* has not been observed.

What is claimed is:

1. A new and distinct cultivar of *Verbena* plant named 'Balazgagic' substantially, as herein shown and described, which:

1. Exhibits purple-colored flowers,
2. Forms cleft, dark green-colored foliage,
3. Exhibits a good basal branching character, and
4. Exhibits a spreading and trailing growth habit.

* * * * *